United States Patent [19]

Mausner

[11] Patent Number: 5,215,759
[45] Date of Patent: Jun. 1, 1993

[54] COSMETIC COMPOSITION

[75] Inventor: Jack Mausner, New York, N.Y.

[73] Assignee: Chanel, Inc., Piscataway, N.J.

[21] Appl. No.: 769,863

[22] Filed: Oct. 1, 1991

[51] Int. Cl.$^5$ .............................. A61K 9/50; A61K 9/52
[52] U.S. Cl. ..................................... 424/489; 424/491; 424/502; 424/499; 424/59; 424/195.1; 424/457; 514/860; 514/847
[58] Field of Search ................................ 424/489–502, 424/450, 457, 401, 195.1, 59; 514/847, 846, 963, 860

[56] References Cited

U.S. PATENT DOCUMENTS

| | | | |
|---|---|---|---|
| 3,697,643 | 10/1972 | Shepherd et al. | 424/63 |
| 3,864,275 | 2/1975 | Kan | 424/497 |
| 3,911,105 | 10/1975 | Papantoniou et al. | 424/64 |
| 3,966,398 | 6/1976 | Vanlerberghe et al. | 8/11 |
| 4,125,549 | 11/1979 | Coopersmith et al. | 260/425 |
| 4,247,411 | 1/1981 | Vanlerberghe | 424/491 |
| 4,369,037 | 1/1983 | Matsunaga et al. | 8/127.51 |
| 4,423,031 | 12/1983 | Murui et al. | 424/63 |
| 4,440,295 | 8/1983 | Ootsu et al. | 252/356 |
| 4,460,371 | 7/1984 | Abber | 604/897 |
| 4,481,186 | 11/1984 | Deckner | 514/847 |
| 4,549,990 | 10/1985 | Seguin et al. | 260/397.25 |
| 4,608,392 | 8/1986 | Jacquet et al. | 514/844 |
| 4,752,496 | 6/1988 | Fellows et al. | 427/27 |
| 4,758,599 | 7/1988 | Minetti | 514/844 |
| 4,820,510 | 4/1989 | Arraudeau et al. | 424/63 |
| 4,883,659 | 11/1989 | Goodman | 514/844 |
| 4,925,667 | 5/1990 | Fellows et al. | 424/401 |
| 4,927,952 | 5/1990 | Gueyne et al. | 556/419 |
| 4,952,560 | 8/1990 | Kigasawa | 514/774 |
| 4,980,155 | 12/1990 | Shah et al. | 424/63 |
| 4,988,502 | 1/1991 | Ounanian et al. | 424/63 |
| 5,034,226 | 7/1991 | Beck | 424/195.1 |
| 5,037,803 | 8/1991 | Gueyne | 514/772 |
| 5,053,220 | 10/1991 | Arraudeau et al. | 424/63 |
| 5,053,221 | 10/1991 | Robertson et al. | 424/63 |
| 5,061,481 | 10/1991 | Suzuki et al. | 424/63 |

*Primary Examiner*—Thurman K. Page
*Assistant Examiner*—Sally Gardner
*Attorney, Agent, or Firm*—Denton L. Anderson

[57] ABSTRACT

A cosmetic composition according to the present invention comprises: water, and emulsified and dispersed in the water: (1) a moisturizing component comprising: (a) hydrophilic microcapsules and (b) lipophilic microcapsules comprising: glycosphingolipids, phospholipids, cholesterol, at least one long-chain saturated fatty acid selected from the group consisting of myristic acid, palmitic acid, stearic acid, and arachidic acid, squalane, a $C_{10}$–$C_{30}$ carboxylic acid ester of a sterol selected from the group consisting of cholesterol, lanosterol, and mixtures thereof, and octyldodecanol; (2) a short-chain fatty acid ester of tocopherol; (3) a glyceryl ester complex; (4) *Aloe vera* gel; and (5) chamomile extract. Each of these ingredients is present in a cosmetically effective quantity. The proportion of hydrophilic microcapsules to lipophilic microcapsules in the moisturizing component is from about 2:3 to about 3:2. The composition preferably further comprises microcapsules comprising methylsilanol elastinate for firming activity, and can additionally comprise caffeine plus microcapsules comprising methylsilanol theophyllinacetate alginate and methylsilanol mannuronate for anti-cellulite activity, along with a number of plant extracts and plant extract-miscible components. A cosmetic composition according to the present invention can further comprise ancillary components.

25 Claims, No Drawings

COSMETIC COMPOSITION

BACKGROUND

This application is directed to an improved cosmetic composition for use on the body.

Aging, along with environmental conditions, such as heating and air conditioning, exposure to the sun, and pollution, exert severe stress on the skin, resulting in dryness of the skin, accumulation of cellulite, wrinkles, and other cosmetically undesirable effects. Although a number of cosmetic compositions for use on the body already exist, there is a need for a simple to apply and effective cosmetic treatment that simultaneously provides multiple functions, including hydration, protection, and soothing of the skin, anti-free radical activity, along with anti-cellulite or firming activity, as appropriate. It is especially desirable that such a treatment can be prepared in alternative formulations that can be modified to meet the particular needs of each user.

SUMMARY

A cosmetic composition according to the present invention meets these needs by providing simultaneously a totally comprehensive skin care system for the body. A cosmetic composition according to the present invention, when applied to the skin, performs multiple simultaneous beneficial functions, including significant hydration, significant protection, calming, and soothing, and anti-free radical activity. The use of a balance of two types of microcapsules, i.e., hydrophilic and lipophilic, will ensure that the composition provides long term, slow release comprehensive moisturizing activity. The composition is additionally formulated with microcapsules providing either firming activity or anti-cellulite activity, or both, again to ensure slow release long term efficacy.

A skin cream composition according to the present invention comprises: water, and emulsified and dispersed in the water:

(1) a moisturizing component comprising:
 (a) hydrophilic microcapsules; and
 (b) lipophilic microcapsules;
(2) a short-chain fatty acid ester of tocopherol selected from the group consisting of tocopheryl acetate, tocopheryl propionate, tocopheryl butyrate, and mixtures thereof;
(3) a glyceryl ester complex;
(4) *Aloe vera* gel; and
(5) chamomile extract.

The hydrophilic microcapsules, the lipophilic microcapsules, the short-chain fatty acid ester of tocopherol, the glyceryl ester complex, the *Aloe vera* gel, and the chamomile extract are each present in a cosmetically effective quantity. The proportion of hydrophilic microcapsules to lipophilic microcapsules in the moisturizing component is from about 2:3 to about 3:2.

Preferably, the hydrophilic microcapsules comprise in water:

(1) glycerin;
(2) chitin;
(3) sodium lactate;
(4) sodium pyrrolidone carboxylate;
(5) glycogen;
(6) urea;
(7) propylene glycol; and
(8) at least one amino acid selected from the group consisting of glycine, arginine, lysine, histidine, and ornithine. The lipophilic microcapsules preferably comprise:

(1) glycosphingolipids;
(2) phospholipids;
(3) cholesterol;
(4) at least one long-chain saturated fatty acid selected from the group consisting of myristic acid, palmitic acid, stearic acid, and arachidic acid;
(5) squalane;
(6) a $C_{10}$–$C_{30}$ carboxylic acid ester of a sterol selected from the group consisting of cholesterol, lanosterol, and mixtures thereof; and
(7) octyldodecanol.

A cosmetic composition according to the present invention can further comprise microcapsules comprising methylsilanol elastinate present in a cosmetically effective quantity. Alternatively, the composition can further comprise caffeine and either microcapsules comprising methylsilanol theophyllinacetate alginate or microcapsules comprising methylsilanol theophyllinacetate alginate and methylsilanol mannuronate, the caffeine and the microcapsules each being present in a cosmetically effective quantity. The composition can comprise both: (1) microcapsules comprising methylsilanol elastinate and (2) caffeine and microcapsules comprising methylsilanol theophyllinacetate alginate and methylsilanol mannuronate.

When the composition comprises caffeine and microcapsules comprising both methylsilanol theophyllinacetate alginate and methylsilanol mannuronate, it preferably further comprises a mixture of plant extracts and plant extract-miscible components comprising: witch hazel; horsetail extract; ivy extract; capsicum extract; a vegetal amino complex comprising from about 25% to about 35% of butcher broom extract, about 25% to about 35% of propylene glycol, about 5% to about 15% each of hydrocotyl extract, horse chestnut extract, and panthenol, about 4% to about 8% of calendula extract, and about 3% to about 6% of yeast extract; and comfrey extract, as well as a long-chain saturated fatty acid ester of ascorbic acid. Both the mixture of plant extracts and plant extract-miscible components and the ester of ascorbic acid are present in a cosmetically effective quantity.

The hydrophilic microcapsules, the lipophilic microcapsules, the short-chain fatty acid ester of tocopherol, the glyceryl ester complex, the *Aloe vera* gel, and the chamomile extract, as well as the microcapsules comprising methylsilanol elastinate or the caffeine and the microcapsules comprising methylsilanol theophyllinacetate alginate, alone or with methylsilanol mannuronate, the mixture of plant extracts and plant-extract miscible components, and the ester of ascorbic acid are all designated the cosmetic components.

Preferably, the hydrophilic microcapsules comprise all of glycine, arginine, lysine, histidine, and ornithine.

The hydrophilic microcapsules can further comprise placental protein, and can also further comprise at least one preservative component selected from the group consisting of phenoxyethanol, chlorphenesin, and methylparaben. Preferably, all of phenoxyethanol, chlorphenesin, and methylparaben are present as preservatives.

The lipophilic microcapsules can further comprise a diglyceryl succinate of a medium-chain fatty acid selected from the group consisting of caprylic acid, capric acid, and mixtures thereof.

Preferably, the moisturizing component comprises from about 0.5% to about 3% of the composition, the short-chain fatty acid ester of tocopherol comprises from about 0.05% to about 1% of the composition, the glyceryl ester complex comprises from about 0.05% to about 2.5% of the composition, the *Aloe vera* gel comprises from about 0.1% to about 1% of the composition, and the chamomile extract comprises from about 0.1% to about 1% of the composition. When microcapsules comprising methylsilanol elastinate are present, they preferably comprise from about from about 0.5% to about 3% of the composition. When caffeine plus microcapsules comprising methylsilanol theophyllinacetate alginate and methylsilanol alginate are present, the caffeine preferably comprises from about 0.5% to about 2% of the composition and the microcapsules comprising methylsilanol theophyllinacetate alginate and methylsilanol mannuronate preferably comprise from about 3% to about 7% of the composition. Preferably, the microcapsules comprising methylsilanol theophyllinacetate alginate and methylsilanol mannuronate comprise from about 40% to about 60% methylsilanol theophyllinacetate and from about 40% to about 60% methylsilanol mannuronate.

A preferred range of compositions for some of the cosmetic components is as follows:

(1) the hydrophilic microcapsules preferably comprise:
   (a) from about 20% to about 40% glycerin;
   (b) from about 10% to about 20% chitin;
   (c) from about 5% to about 15% sodium lactate;
   (d) from about 5% to about 15% sodium pyrrolidone carboxylate;
   (e) from about 1% to about 5% each of glycogen, urea, propylene glycol, and sodium chloride;
   (f) up to about 1% each of glycine, arginine, lysine, histidine, ornithine, placental protein, phenoxyethanol, and chlorphenesin; and
   (g) up to about 0.5% of methylparaben;

(2) the lipophilic microcapsules preferably comprise:
   (a) from about 5% to about 15% each of glycosphingolipids, phospholipids, and cholesterol;
   (b) from about 1% to about 5% each of stearic acid, palmitic acid, squalane, and a $C_{10}$–$C_{30}$ carboxylic acid ester of a sterol selected from the group consisting of cholesterol, lanosterol, and mixtures thereof;
   (c) up to about 1% of a diglyceryl succinate of a medium-chain fatty acid selected from the group consisting of caprylic acid, capric acid, and mixtures thereof; and
   (d) from about 60% to about 80% of octyldodecanol;
   the moisturizing component comprising from about 0.5% to about 3% of the composition;

(3) the short-chain fatty acid ester of tocopherol preferably comprises from about 0.5% to about 1% of the composition;

(4) the glyceryl ester complex preferably comprises from 0.5% to about 2.5% of the composition;

(5) the *Aloe vera* gel preferably comprises from about 0.1% to about 1% of the composition;

(6) the chamomile extract comprises from about 0.1% to about 1% of the composition. Preferred ranges for each component of the mixture of plant extracts and plant extract-miscible components and for the ester of ascorbate are given below in connection with the ingredients of a preferred cosmetic composition of the present invention intended for use as a cellulite firming gel.

In addition to the cosmetic components, a cosmetic composition according to the present invention can comprise additional ancillary components. These ancillary components can include at least one of: (1) a solvent component; (2) a preservative component; (3) trisodium EDTA; (4) an emulsifier component; (5) a cationic dimethyldiallyl ammonium chloride homopolymer; (6) fragrance; (7) polyethylene; (8) pigment; (9) a lipid-soluble component; (10) a thickener component; (11) a complex of dextran, glycine, and glucosamine; (12) a glycosaminoglycan complex; (13) magnesium aluminum silicate; (14) a cross-polymer of acrylates and $C_{10}$–$C_{30}$ alkyl acrylate; (15) methylnicotinate; and (16) triethanolamine.

A preferred cosmetic composition according to the present invention, intended for use as an exfoliating body slougher, comprises: water, and emulsified and dispersed in the water:

(1) a moisturizing component comprising:
   (a) hydrophilic microcapsules comprising from about 0.5% to about 3% of the composition, the hydrophilic microcapsules comprising in water:
      (i) about 20% to about 40% glycerin;
      (ii) about 10% to about 20% chitin;
      (iii) about 5% to about 15% each of sodium lactate and sodium pyrrolidone carboxylic acid;
      (iv) about 1% to about 5% each of glycogen, urea, propylene glycol, and sodium chloride;
      (v) up to about 1% each of glycine, arginine, lysine, histidine, and ornithine, such that at least one amino acid is present in the hydrophilic microcapsules;
      (vi) up to about 1% each of placental protein, phenoxyethanol, and chlorphenesin; and
      (vii) up to about 0.5% of methylparaben; and
   (b) lipophilic microcapsules comprising from about 0.5% to about 3% of the composition, the lipophilic microcapsules comprising:
      (i) about 5% to about 15% each of glycosphingolipids, phospholipids, and cholesterol;
      (ii) about 1% to about 5% each of stearic acid, palmitic acid, squalane, and a $C_{10}$–$C_{30}$ carboxylic acid ester of a sterol selected from the group consisting of cholesterol, lanosterol, and mixtures thereof;
      (iii) up to about 1% of a diglyceryl succinate of a medium-chain fatty acid selected from the group consisting of caprylic acid, capric acid, and mixtures thereof; and
      (iv) about 60% to about 80% of octyldodecanol;
      the quantities of hydrophilic microcapsules and lipophilic microcapsules being such that the ratio of hydrophilic microcapsules to lipophilic microcapsules is from about 2:3 to about 3:2;

(2) about 0.5% to about 3% of microcapsules comprising methylsilanol elastinate;

(3) about 2.55% to about 3.45% of 1,3-butylene glycol;

(4) about 2.1% to about 2.9% of a complex of propylene glycol, phenoxyethanol, chlorphenesin, and methylparaben, wherein the propylene glycol comprises from about 30% to about 45% of the complex, the phenoxyethanol comprises from about 22% to about 37% of the complex, the chlorphenesin comprises from about 11% to about 22% of the complex, and the methylparaben comprises from about 11% to about 22% of the complex;
(5) about 0.01% to about 0.1% of trisodium EDTA;
(6) about 2.4% to about 3.2% of magnesium aluminum silicate;
(7) about 11.5% to about 15.5% of a complex of glyceryl stearate and PEG-100 stearate, wherein the glyceryl stearate comprises from about 40% to about 60% of the complex and the PEG-100 stearate comprises from about 40% to about 60% of the complex;
(8) about 0.05% to about 0.15% of tocopheryl acetate;
(9) about 0.05% to about 0.15% of a glyceryl ester complex comprising about 65% to about 85% of glyceryl linoleate, about 5% to about 15% of glyceryl linolenate, and about 1% to about 5% of glyceryl arachidonate;
(10) about 13.6% to about 18.4% of a complex comprising disodium cocoamphodiacetate, sodium trideceth sulfate, and hexylene glycol;
(11) about 17% to about 23% of a complex comprising disodium cocoamphodiacetate, sodium lauryl sulfate, sodium laureth sulfate, and propylene glycol;
(12) about 0.35% to about 0.65% of a cationic dimethyldiallyl ammonium chloride homopolymer;
(13) about 0.35% to about 0.65% of *Aloe vera* gel;
(14) about 0.35% to 0.65% of chamomile extract;
(15) about 0.35% to about 0.65% of fragrance;
(16) about 12% to about 16% of polyethylene; and
(17) about 0.01% to about 0.05% of FD & C Blue No.

Another preferred cosmetic composition according to the present invention, intended for use as a moisturizing body lotion, comprises: water, and emulsified and dispersed in the water:
(1) a moisturizing component comprising:
  (a) hydrophilic microcapsules, the hydrophilic microcapsules comprising from about 0.5% to about 3% of the composition, the hydrophilic microcapsules comprising in water:
    (i) about 20% to about 40% glycerin;
    (ii) about 10% to about 20% chitin;
    (iii) about 5% to about 15% each of sodium lactate and sodium pyrrolidone carboxylic acid;
    (iv) about 1% to about 5% each of glycogen, urea, propylene glycol, and sodium chloride;
    (v) up to about 1% each of glycine, arginine, lysine, histidine, and ornithine, such that at least one amino acid is present in the hydrophilic microcapsules;
    (vi) up to about 1% each of placental protein, phenoxyethanol, and chlorphenesin; and
    (vii) up to about 0.5% of methylparaben; and
  (b) lipophilic microcapsules comprising from about 0.5% to about 3% of the composition, the lipophilic microcapsules comprising:
    (i) about 5% to about 15% each of glycosphingolipids, phospholipids, and cholesterol;
    (ii) about 1% to about 5% each of stearic acid, palmitic acid, squalane, and a $C_{10}$–$C_{30}$ carboxylic acid ester of a sterol selected from the group consisting of cholesterol, lanosterol, and mixtures thereof;
    (iii) up to about 1% of a diglyceryl succinate of a medium-chain fatty acid selected from the group consisting of caprylic acid, capric acid, and mixtures thereof; and
    (iv) about 60% to about 80% of octyldodecanol; the quantities of hydrophilic microcapsules and lipophilic microcapsules being such that the ratio of hydrophilic microcapsules to lipophilic microcapsules is from about 2:3 to about 3:2;
(2) about 0.5% to about 3% of microcapsules comprising methylsilanol elastinate;
(3) about 0.4% to about 0.6% of tocopheryl acetate;
(4) about 1.7% to about 2.3% of steareth-2;
(5) about 1.7% to about 2.3% of steareth-21;
(6) about 0.4% to about 0.6% of methylgluceth-20 sesquistearate;
(7) about 1.7% to about 2.3% of cetyl alcohol;
(8) about 3.4% to about 4.6% of jojoba oil; (i) about 5.5% to about 7.5% of benzoic acid ester of $C_{12}$–$C_{15}$ alcohol;
(9) about 1.7% to about 2.3% of PPG-14 butyl ether;
(10) about 0.15% to about 0.25% of dimethicone;
(11) about 2.55% to about 3.45% of a complex of sphingolipids, phospholipids, and octyldodecanol, wherein the sphingolipids comprise about 60% to about 80% of the complex, the phospholipids comprise from about 10% to about 19% of the complex, and the octyldodecanol comprises from about 10% to about 19% of the complex;
(12) about 1.7% to about 2.3% of a glyceryl ester complex comprising about 65% to about 85% of glyceryl linoleate, about 5% to about 15% of glyceryl linolenate, and about 1% to about 5% of glyceryl arachidonate;
(13) about 3.4% to about 4.6% of PPG-15 stearyl ether;
(14) about 2.1% to about 2.9% of a complex of propylene glycol, phenoxyethanol, chlorphenesin, and methylparaben, wherein the propylene glycol comprises from about 30% to about 45% of the complex, the phenoxyethanol comprises from about 22% to about 37% of the complex, the chlorphenesin comprises from about 11% to about 22% of the complex, and the methylparaben comprises from about 11% to about 22% of the complex;
(15) about 4.25% to about 5.75% of propylene glycol;
(16) about 0.34% to about 0.46% of xanthan gum;
(17) about 2.55% to about 3.45% of a complex of dextran, glycine, and glucosamine, wherein the dextran comprises from about 70% to about 90% of the complex, the glycine comprises from about 10% to about 20% of the complex, and the glucosamine comprises from about 5% to about 15% of the complex;
(18) about 2.55% to about 3.45% of a glycosaminoglycan complex;
(19) about 0.4% to about 0.6% of *Aloe vera* gel;
(20) about 0.4% to about 0.6% of chamomile extract; and
(21) about 0.2% to about 0.4% of fragrance.

Yet another preferred cosmetic composition according to the present invention, intended for use as a cellulite firming gel, comprises: water, and emulsified and dispersed in the water:
(1) a moisturizing component comprising:
  (a) hydrophilic microcapsules comprising from about 0.5% to about 3% of the composition, the hydrophilic microcapsules comprising in water:
    (i) from about 20% to about 40% glycerin;

(ii) from about 10% to about 20% chitin;
(iii) from about 5% to about 15% each of sodium lactate and sodium pyrrolidone carboxylate;
(iv) from about 1% to about 5% each of glycogen, urea, propylene glycol, and sodium chloride;
(v) up to about 1% each of glycine, arginine, lysine, histidine, and ornithine, such that at least one amino acid is present in the hydrophilic microcapsules;
(vi) up to about 1% each of placental protein, phenoxyethanol, and chlorphenesin; and
(vii) up to about 0.5% of methylparaben; and
(b) lipophilic microcapsules comprising from about 0.5% to about 3% of the composition, the lipophilic microcapsules comprising:
(i) from about 5% to about 15% each of glycosphingolipids, phospholipids, and cholesterol;
(ii) from about 1% to about 5% each of stearic acid, palmitic acid, squalene, and a $C_{10}$—$C_{30}$ carboxylic acid ester of a sterol selected from the group consisting of cholesterol, lanosterol, and mixtures thereof; and
(iii) up to about 1% of a diglyceryl succinate of a medium-chain fatty acid selected from the group consisting caprylic acid, capric acid, and mixtures thereof; and
(iv) from about 60% to about 80% of octyldodecanol;
the quantities of hydrophilic microcapsules and lipophilic microcapsules being such that the ratio of hydrophilic microcapsules to lipophilic microcapsules is from about 2:3 to about 3:2;
(2) from about 0.4% to about 0.6% of tocopheryl acetate;
(3) from about 0.4% to about 0.6% of a glyceryl ester complex comprising from about 65% to about 85% of glyceryl linoleate, from about 5% to about 15% of glyceryl linolenate, and from about 1% to about 5% of glyceryl arachidonate;
(4) from about 0.4% to about 0.6% of *Aloe vera* gel;
(5) from about 0.4% to about 0.6% of chamomile extract;
(6) from about 0.5% to about 3% of microcapsules comprising methylsilanol elastinate;
(7) from about 3% to about 7% of microcapsules comprising in water:
(a) from about 40% to about 60% methylsilanol theophyllinacetate alginate; and
(b) from about 40% to about 60% methylsilanol mannuronate;
(8) from about 0.5% to about 2% of caffeine;
(9) from about 4.25% to about 5.75% of witch hazel;
(10) from about 0.85% to about 1.15% of horsetail extract;
(11) from about 0.85% to about 1 15% of ivy extract;
(12) from about 2.55% to about 3.45% of capsicum extract;
(13) from about 0.85% to about 1.15% of a vegetal amino complex comprising from about 25% to about 35% of butcher broom extract, from about 25% to about 35% of propylene glycol, from about 5% to about 15% each of hydrocotyl extract, horse chestnut extract, and panthenol, from about 4% to about 8% of calendula extract, and from about 3% to about 6% of yeast extract;
(14) from about 0.85% to about 1.15% of ascorbyl palmitate;
(15) from about 0.73% to about 0.98% of a crosspolymer of acrylates and $C_{10}$-$C_{30}$ alkyl acrylate;
(16) from about 0.35% to about 0.55% of carrageenan;
(17) from about 0.25% to about 0.45% of xanthan gum;
(18) from about 5% to about 7% of 1,3-butylene glycol;
(19) from about 3.4% to about 4.6% of PPG-1-isoceteth-3-acetate;
(20) from about 4.2% to about 5.75% of laureth-2-benzoate;
(21) from about 1.25% to about 1.75% of diisostearyl dimer dilinoleate;
(22) from about 1.25% to about 1.75% of isodecyl oleate;
(23) from about 3.4% to about 4.6% of myristyl octanoate;
(24) from about 0.1% to about 0.3% of ascorbyl palmitate;
(25) from about 1.7% to about 2.3% of glyceryl stearate;
(26) from about 0.64% to about 0.8% of a complex of phenoxyethanol, methylparaben, ethylparaben, propylparaben, and butylparaben, with the phenoxyethanol comprising from about 60% to about 80% of the complex, the methylparaben comprising from about 13% to about 17% of the complex, and the ethylparaben, propylparaben, and butylparaben each comprising from about 4% to about 6% of the complex;
(27) from about 0.05% to about 0.1% of methylnicotinate;
(28) from about 0.1% to about 0.2% of triethanolamine; and
(29) from about 0.2% to about 0.6% of fragrance.

DESCRIPTION

A new combination of ingredients results in a cosmetic composition for use on the body that, in its basic formulation, provides simultaneously a totally comprehensive hydration, i.e., addressing both water shortage and lipid shortage, protection, calming, and soothing of the skin, and anti-free radical activity, as well as cellulite firming where necessary. The basic formulation of a cosmetic composition according to the present invention comprises an aqueous base in which cosmetic components are emulsified and dispersed. The cosmetic components necessarily include at least two types of microcapsules, hydrophilic microcapsules and lipophilic microcapsules, together with a short-chain fatty acid ester of tocopherol, a glyceryl ester complex, *Aloe vera* gel, and chamomile extract. Each of the ingredients is present in a cosmetically effective quantity. The hydrophilic and lipophilic microcapsules together comprise a totally comprehensive moisturizing component, addressing both water and lipid shortages, in contrast to previous moisturizers that generally address either one or the other.

Preferably, a cosmetic composition according to the present invention further comprises in a cosmetically effective quantity: (1) microcapsules comprising methylsilanol elastinate to exert firming activity or (2) caffeine and microcapsules exerting anti-cellulite activity. The microcapsules exerting anti-cellulite activity preferably comprise methylsilanol theophyllinacetate alginate and methylsilanol mannuronate in water; less preferably, microcapsules comprising methylsilanol theophyllinacetate alginate alone in water can be used to exert anti-cellulite activity. The composition can comprise both microcapsules exerting firming activity and microcapsules exerting anti-cellulite activity. When the composition comprises microcapsules exerting anti-cellulite activity, it preferably further comprises a mixture of plant extracts and plant extract-miscible components comprising: (1) witch hazel; (2) horsetail extract; (3) ivy extract; (4) capsicum extract; (5) a vegetal amino complex comprising from about 25% to about 35% of butcher broom extract, about 25% to about 35% of propylene glycol, about 5% to about 15% each of hydrocotyl extract, horse chestnut extract, and panthenol, about 4% to about 8% of calendula extract, and about 3% to about 6% of yeast extract; and (6) comfrey extract. It preferably further comprises a long-chain saturated fatty acid ester of ascorbic acid. Each component of the mixture of plant extracts and plant extract-miscible components is present in a cosmetically effective quantity, as is the long-chain fatty acid ester of ascorbic acid.

Optimally, a cosmetic composition according to the present invention also comprises ancillary components such as: (1) a solvent component; (2) a preservative component; (3) trisodium EDTA; (4) an emulsifier component; (5) a cationic dimethyldiallyl ammonium chloride homopolymer; (6) fragrance; (7) polyethylene; (8) pigment; (9) a lipid-soluble component; (10) a thickener component; (11) a complex of dextran, glycine, and glucosamine; (12) a glycosaminoglycan complex; (13) magnesium aluminum silicate; (14) a cross-polymer of acrylates and $C_{10}$-$C_{10}$ alkyl acrylate; (15) methylnicotinate; and (16) triethanolamine.

The ingredients are dispersed in an emulsified composition by the method of preparation discussed below. "Dispersal" refers to any process by which the ingredients are uniformly distributed in the emulsified base and includes dissolving, emulsifying, and forming a colloidal suspension.

I. NATURE AND PROPORTION OF INGREDIENTS OF THE COSMETIC COMPOSITION

A. The Cosmetic Components

The cosmetic components include: (1) hydrophilic microcapsules; (2) lipophilic microcapsules; (3) a short-chain fatty acid ester of tocopherol; (4) a glyceryl ester complex; (5) *Aloe vera* gel; (6) chamomile extract; (7) optionally, microcapsules comprising methylsilanol elastinate; (8) optionally, caffeine plus either (a) microcapsules comprising methylsilanol theophyllinacetate alginate and methylsilanol mannuronate; or, less preferably, (b) microcapsules comprising methylsilanol theophyllinacetate alginate alone; (9) preferably, when the composition comprises microcapsules comprising methylsilanol theophyllinacetate alginate and methylsilanol mannuronate, a mixture of plant extracts and other plant extract-miscible components comprising: (a) witch hazel; (b) horsetail extract; (c) ivy extract; (d) capsicum extract; (e) a vegetal amino complex comprising from about 25% to about 35% of butcher broom extract, about 25% to about 35% of propylene glycol, about 5% to about 15% each of hydrocotyl extract, horse chestnut extract, and panthenol, about 4% to about 8% of calendula extract, and about 3% to about 6% of yeast extract; (f) comfrey extract; and (10) preferably, when the composition comprises microcapsules comprising methylsilanol theophyllinacetate alginate and methylsilanol mannuronate, a long-chain saturated fatty acid ester of ascorbic acid.

1. The Hydrophilic Microcapsules

The hydrophilic microcapsules have a basic structure consisting of a microporous matrix of a polystyrene derived copolymer and enclosed water in which water-miscible compounds are dissolved and/or dispersed. The microcapsules are about 100 nm in diameter.

The hydrophilic microcapsules preferably comprise in water: (1) glycerin; (2) chitin; (3) sodium lactate; (4) sodium chloride; (5) sodium pyrrolidone carboxylate; (6) glycogen; (7) urea; (8) propylene glycol; and (9) at least one amino acid selected from the group consisting of glycine, arginine, lysine, histidine, and ornithine. Optionally, the hydrophilic microcapsules can further comprise: (10) placental protein; and (11) at least one preservative component selected from the group consisting of phenoxyethanol, chlorphenesin, and methylparaben. Preferably, all of the amino acids glycine, arginine, lysine, histidine, and ornithine are present in the hydrophilic microcapsules. Preferably all of phenoxyethanol, chlorphenesin, and methylparaben are also present in the hydrophilic microcapsules.

A preferred range of compositions for the hydrophilic microcapsules is as follows: glycerin, from about 20% to about 40%; chitin, from about 10% to about 20%; sodium lactate and sodium pyrrolidone carboxylate, from about 5% to about 15% each; glycogen, urea, propylene glycol, and sodium chloride, from about 1% to about 5% each; glycine, arginine, lysine, histidine, ornithine, placental protein, phenoxyethanol, and chlorphenesin, up to about 1% each; methylparaben, up to about 0.5%; and water, from about 15% to about 25%.

2. The Lipophilic Microcapsules

The lipophilic microcapsules have a basic structure consisting of a coated core structure obtained by a controlled polymerization of polysiloxane, leading to a tridimensional lattice, coated by a polymeric shell. The lipophilic microcapsules are about 100 nm in diameter.

The lipophilic microcapsules preferably comprise: (1) octyldodecanol; (2) glycosphingolipids; (3) phospholipids; (4) cholesterol; (5) at least one long-chain saturated fatty acid selected from the group consisting of myristic acid, palmitic acid, stearic acid, and arachidic acid; (6) squalane; (7) a $C_{10}$-$C_{30}$ carboxylic acid ester of a sterol selected from the group consisting of cholesterol, lanosterol, and mixtures thereof; and (8) optionally, a diglyceryl succinate of a medium-chain fatty acid selected from the group consisting caprylic acid, capric acid, and mixtures thereof.

Glycosphingolipids comprise ceramide covalently bound to carbohydrate on the primary hydroxyl group of the ceramide. The carbohydrate is typically glucose, lactose, N-acetylglucosamine, N-acetylgalactosamine, or sialic acid.

The phospholipids can be phosphatidyl ethanolamine, phosphatidyl choline, phosphatidyl serine, phosphatidyl inositol, or diphosphatidyl glycerol.

Preferably, the long-chain fatty acids are palmitic acid and stearic acid. A preferred range of compositions for the lipophilic microcapsules is: octyldodecanol, from about 60% to about 80%; glycosphingolipids, phospholipids, and cholesterol, from about 5% to about 15% each; stearic acid, palmitic acid, squalane, and $C_{10}$-$C_{30}$ carboxylic acid ester of a sterol, from about 1% to about 5% each; and the diglyceryl succinate of a medium-chain fatty acid, up to about 1%.

The moisturizing component (hydrophilic microcapsules plus lipophilic microcapsules) preferably comprises from about 0.5% to about 3% of a composition according to the present invention. The ratio between hydrophilic microcapsules and lipophilic microcapsules in the moisturizing component is from about 2:3 to about 3:2.

Although applicant does not intend to be bound by this theory, it is believed that the use of both hydrophilic and lipophilic microcapsules provides a moisturizing effect while at the same time preventing depletion of the essential oils of the skin. In addition, the encapsulation of the active ingredients provides slow release and, therefore, long-lasting effects of the active ingredients.

3. The Short-Chain Fatty Acid Ester of Tocopherol

The short-chain fatty acid ester of tocopherol can be selected from the group consisting of tocopheryl acetate, tocopheryl propionate, tocopheryl butyrate, and mixtures thereof. Preferably, the short-chain fatty acid ester of tocopherol is tocopheryl acetate. Preferably, the tocopheryl acetate comprises from about 0.05% to about 1% of the composition; most preferably, from about 0.05% to about 0.6% of the composition. 4. The Glyceryl Ester Complex The glyceryl ester complex comprises glyceryl linoleate, glyceryl linolenate, and glyceryl arachidonate. Preferably, the glyceryl ester complex comprises about 65% to about 85% glyceryl linoleate, about 5% to about 15% glyceryl linolenate, and about 1% to about 5% glyceryl arachidonate. Preferably, the glyceryl ester complex comprises from about 0.05% to about 2.5% of the composition; most preferably, from about 0.05% to about 2.3% of the composition.

5. The Aloe vera Gel

The *Aloe vera* gel preferably comprises from about 0.1% to about 1% of the composition, most preferably from about 0.35% to about 0.65% of the composition. The *Aloe vera* gel imparts a soothing and calming effect on the skin.

6. The Chamomile Extract

The chamomile extract preferably comprises from about 0.1% to 1% of the composition, most preferably from about 0.35% to about 0.65% of the composition. The chamomile extract also imparts a soothing and calming effect on the skin.

7. The Methylsilanol Elastinate Microcapsules

A cosmetic composition according to the present invention can additionally comprise microcapsules comprising an aqueous solution of methylsilanol elastinate. The microcapsules have a basic structure of a microporous matrix of a polystyrene derived copolymer. Methylsilanol elastinate is a derivative of the fibrous protein elastin, a major component of skin. Although applicant does not intend to be bound by this theory, it is believed that microcapsules containing methylsilanol elastinate exert a firming effect on the skin. If present, the microcapsules containing methylsilanol elastinate preferably comprise from about 0.5% to about 3% of the composition.

8. The Methylsilanol Theophyllinacetate Alginate Microcapsules

A cosmetic composition according to the present invention can comprise microcapsules comprising an aqueous solution of methylsilanol theophyllinacetate alginate. It believed that microcapsules containing methylsilanol theophyllinacetate alginate exert an anti-cellulite action upon the skin. Preferably, the microcapsules further comprise an aqueous solution of methylsilanol mannuronate; most preferably, the microcapsules comprises from about 40% to about 60% of methylsilanol theophyllinacetate alginate and about 40% to about 60% of methylsilanol mannuronate. If present, the microcapsules comprising methylsilanol theophyllinacetate alginate and methylsilanol mannuronate preferably comprises from about 3% to about 7% of the composition.

In a less preferred alternative, the composition can comprise microcapsules comprising an aqueous solution of methylsilanol theophyllinacetate alginate alone. If used, these microcapsules can comprise from about 0.5% to about 3% of the composition.

9. Caffeine

The cosmetic composition according to the present invention comprising microcapsules containing an aqueous solution of methylsilanol theophyllinacetate alginate, whether alone or with methylsilanol mannuronate, further comprises caffeine in a cosmetically effective quantity. The caffeine preferably comprises from about 0.5% to about 2% of the composition.

10. The Plant Extract Mixture

When the composition comprises microcapsules containing methylsilanol theophyllinacetate alginate and methylsilanol mannuronate, it preferably further comprises a mixture of plant extracts and other components comprising: (1) witch hazel; (2) horsetail extract; (3) ivy extract; (4) capsicum extract; (5) a vegetal amino complex comprising from about 25% to about 35% of butcher broom extract, about 25% to about 35% of propylene glycol, about 5% to about 15% each of hydrocotyl extract, horse chestnut extract, and panthenol, about 4% to about 8% of calendula extract, and about 3% to about 6% of yeast extract; and (6) comfrey extract, each in a cosmetically effective quantity. A suitable vegetal amino complex is LS-2376, marketed by Lab Serobiologique, Somerville, N.J. Most preferably, the composition comprises from about 4.25% to about 5.75% of witch hazel, about 0.85% to about 1.15% of horsetail extract, about 0.85% to about 1.15% of ivy extract, about 2.55% to about 3.45% of capsicum extract, about 0.85% to about 1.15% of vegetal amino complex, and about 0.85% to about 1.15% of comfrey extract.

11. The Long-chain Fatty Acid Ester of Ascorbic Acid

When the composition comprises microcapsules containing methylsilanol theophyllinacetate alginate and methylsilanol mannuronate, it preferably further also comprises a long-chain fatty acid ester of ascorbate. The long-chain fatty acid ester of ascorbate can be selected from the group consisting of ascorbyl myristate, ascorbyl palmitate, ascorbyl stearate, and mixtures thereof. Preferably, the long-chain fatty ester of ascorbate is ascorbyl palmitate. Most preferably, the composition contains from about 0.01% to about 0.03% of ascorbyl palmitate.

B. The Ancillary Components

The ancillary components, whose use is optional but preferable, impart additional desirable properties to a cosmetic composition according to the present invention. These components can include: (1) a solvent component; (2) a preservative component; (3) trisodium EDTA; (4) an emulsifier component; (5) a cationic dimethyldiallyl ammonium chloride homopolymer; (6) fragrance; (7) polyethylene; (8) pigment; (9) a lipid-soluble component; (10) a thickener component; (11) a complex of dextran, glycine, and glucosamine; (12) a glycosaminoglycan complex; (13) magnesium aluminum silicate; (14) a cross-polymer of acrylates and $C_{10}$–$C_{30}$ alkyl acrylate; (15) methylnicotinate; and (16) triethanolamine.

As discussed below, various cosmetic compositions according to the present invention comprise different combinations of ancillary components.

1. The Solvent Component

The cosmetic composition can comprise a solvent component for greater uniformity and ease of preparation. The solvent component can be selected from the group consisting of propylene glycol, 1,3-butylene glycol, and mixtures thereof. In one composition according to the present invention, intended for use as an exfoliating body slougher, the solvent component is preferably 1,3-butylene glycol and most preferably comprises about 2.55% to about 3.45% of the composition. In a second composition according to the present invention, intended for use as a moisturizing body lotion, the solvent component is preferably propylene glycol and most preferably comprises about 4.25% to about 5.75% of the composition.

2. The Preservative Component

The composition can further comprise a preservative component to retard microbial and mold growth in the composition, which is typically manufactured under clean but non-sterile conditions. The preservative component can comprise either: (1) a complex of propylene glycol, phenoxyethanol, chlorphenesin, and methylparaben; or (2) a complex of phenoxyethanol, methylparaben, ethylparaben, propylparaben, and butylparaben.

In the complex of propylene glycol, phenoxyethanol, chlorphenesin, and methylparaben, the propylene glycol comprises from about 30% to about 45% of the complex, the phenoxyethanol comprises from about 22% to about 37% of the complex, the chlorphenesin comprises from about 11% to about 22% of the complex, and the methylparaben comprises from about 11% to about 22% of the complex. A suitable complex of propylene glycol, phenoxyethanol, chlorphenesin, and methylparaben is available as Elestab 388 from Lab Serobiologique of Somerville, N.J. In the compositions according to the present invention intended for use as an exfoliating body slougher and as a moisturizing body lotion, this complex preferably comprises from about 2.1% to about 2.9% of the composition.

In the complex of phenoxyethanol, methylparaben, ethylparaben, propylparaben, and butylparaben, the phenoxyethanol comprises from about 60% to about 80% of the complex, the methylparaben comprises from about 13% to about 17% of the complex, and the ethylparaben, propylparaben, and butylparaben each comprise from about 4% to about 6% of the complex. A suitable complex of phenoxyethanol, methylparaben, ethylparaben, propylparaben, and butylparaben is available from Nipa Laboratories, Inc., Wilmington, Del., under the name Phenonip TM. In the composition according to the present invention intended for use as a cellulite firming gel, this complex preferably comprises from about 0.64% to about 0.86% of the composition.

3. Trisodium EDTA

A cosmetic composition according to the present invention can further comprise trisodium EDTA to enhance the shelf life of the composition. For the exfoliating body slougher, trisodium EDTA preferably comprises from about 0.01% to about 0.1% of the composition.

4. The Emulsifier Component

A cosmetic composition according to the present invention can further comprise an emulsifier component for greater homogeneity of the composition. The emulsifier can comprise at least one of: (a) a complex of disodium cocoamphodiacetate, sodium lauryl sulfate, sodium laureth sulfate, and propylene glycol; and (b) a complex of disodium cocoamphodiacetate, sodium trideceth sulfate, and hexylene glycol. In the exfoliating body slougher, the emulsifier component preferably comprises both complexes.

A suitable complex of disodium cocoamphodiacetate, sodium lauryl sulfate, sodium laureth sulfate, and propylene glycol is marketed by Rhone-Poulenc, Inc. of Dayton, N.J., under the name of "Miranol 2 MCT." This complex contains from about 20% to about 30% of disodium cocoamphodiacetate, about 7% to about 15% of sodium lauryl sulfate, about 5% to about 10% of sodium laureth sulfate, about 7% to about 15% of propylene glycol, and about 40% to about 60% of water.

A suitable complex of disodium cocoamphodiacetate, sodium trideceth sulfate, and hexylene glycol is marketed by Rhone-Poulenc under the name of "Miranol 2 MCAS." This complex contains from about 20% to about 30% of disodium cocoamphodiacetate, about 15% to about 25% of sodium trideceth sulfate, about 7% to about 15% of hexylene glycol, and about 40% to about 60% of water.

5. The Cationic Dimethyldiallyl Ammonium Chloride Homopolymer

A cosmetic composition according to the present invention can further comprise a 40% aqueous solution of a cationic dimethyldiallyl ammonium chloride homopolymer. A suitable homopolymer preparation is Merquat 110, also known as Polyquaternium-6, and available from Calgon Corp., Water Management Division, Pittsburgh, Pa. For the exfoliating body slougher, the solution of the cationic homopolymer preferably comprises from about 0.35% to about 0.65% of the composition.

6. Fragrance

A cosmetic composition according to the present invention can further comprise fragrance. The fragrance used is a conventional cosmetic fragrance chosen to impart the desired olfactory properties to the cosmetic composition and is chosen to be safe and nonallergenic to the wearer. The use of fragrance is well known in the cosmetic art.

For the exfoliating body slougher, the fragrance preferably comprises from about 0.35% to about 0.65% of the composition; for the moisturizing body lotion, the fragrance preferably comprises from about 0.25% to 0.4% of the composition.

7. Polyethylene

A cosmetic composition according to the present invention can also comprise polyethylene in the form of beads or granules. For the exfoliating body slougher, the polyethylene preferably comprises from about 12% to about 16% of the composition.

8. Pigment

A cosmetic composition according to the present invention can further comprise one or more pigments to impart the desired shade or color to the composition. The use of pigments is well known in the cosmetic art; the pigment used is chosen to be nonallergenic and safe for the user of the cosmetic composition. For the exfoliating body slougher, the pigment is preferably FD&C Blue No. 1 and comprises about 0.01% to about 0.05% of the composition.

9. The Lipid-Soluble Component

The lipid-soluble component can comprise at least one of the following ingredients: (a) steareth-2; (b) steareth-21; (c) methylgluceth-20 sesquistearate; (d) cetyl alcohol; (e) jojoba oil; (f) benzoic acid ester of $C_{12}$–$C_{15}$ alcohols; (g) PPG-14 butyl ether; (h) PPG-15 stearyl ether; (i) dimethicone; (j) a complex of sphingolipids, phospholipids, and octyldodecanol; (k) a complex of glyceryl stearate and PEG-100 stearate; (l) PPG-1-isoceteth-3-acetate; (m) laureth-2- benzoate; (n) diisostearyl dimer dilinoleate; (o) a long-chain cis-monounsaturated fatty acid ester of a medium-chain alcohol; (p) a medium-chain saturated fatty acid ester of a long-chain alcohol; and (q) a long-chain fatty acid ester of glycerol.

Steareth-2 is polyoxyethylene (2) stearyl ether with 0.01% butylated hydroxyanisole and 0.005% citric acid added as preservatives. Similarly, steareth-21 is polyoxyethylene (21) stearyl ether with 0.01% butylated hydroxyanisole and 0.005% citric acid. Methylgluceth-20 sesquistearate is the 20-propoxylate of methylglucoside and has a cyclohexane ring structure.

The complex of sphingolipids, phospholipids, and octyldodecanol comprises from about 10% to about 19% of sphingolipids, about 10% to about 19% of phospholipids, and about 60% to about 80% of octyldodecanol. A suitable complex is marketed by Lab Serobiologique, Inc., of Somerville, N.J., under the name of "Ceramides LS-2303."

The complex of glyceryl stearate and PEG-100 stearate comprises about 40% to about 60% of glyceryl stearate and about 40% to about 60% of PEG-100 stearate. A suitable complex is marketed by ICI Americas, Inc., Specialty Chemicals Division, of Wilmington, Del. under the name of "Arlacel 165."

For the exfoliating body slougher, the lipid-soluble component preferably comprises the complex of glyceryl stearate and PEG-100 stearate; most preferably, the complex of glyceryl stearate and PEG-100 stearate comprises from about 11.5% to about 15.5% of the composition.

For the moisturizing body lotion, the lipid-soluble component preferably comprises steareth-2; steareth-21; methylgluceth-20 sesquistearate; cetyl alcohol; jojoba oil; benzoic acid ester of $C_{12}$–$C_{15}$ alcohols; PPG-14 butyl ether; dimethicone; the complex of sphingolipids, phospholipids, and octyldodecanol; and PPG-15 stearyl ether. Most preferably, the steareth-2, steareth-21, cetyl alcohol, and PPG-14 butyl ether each comprise from about 1.7% to about 2.3% of the composition; the methylgluceth-20 sesquistearate comprises from about 0.4% to about 0.6% of the composition; the jojoba oil and the PPG-15 stearyl ether each comprise from about 3.4% to about 4.6% of the composition; the benzoic acid ester of $C_{12}$–$C_{15}$ alcohols comprise about 5.5% to about 7.5% of the composition; the dimethicone comprises from about 0.15% to about 0.25% of the composition; and the complex of sphingolipids, phospholipids, and octyldodecanol comprises about 2.55% to about 3.45% of the composition.

For the cellulite firming gel, the lipid-soluble component preferably comprises PPG-1-isoceteth-3-acetate, laureth-2-benzoate, diisostearyl dimer dilinoleate, isodecyl oleate, myristyl octanoate, and glyceryl stearate. Most preferably, the PPG-1-isoceteth-3-acetate comprises from about 3.4% to about 4.6% of the composition, the laureth-2-benzoate comprises from about 4.25% to about 5.75% of the composition, the diisostearyl dimer dilinoleate and the isodecyl oleate each comprise from about 1.25% to about 1.75% of the composition, the myristyl octanoate comprises from about 3.4% to about 4.6% of the composition, and the glyceryl stearate comprises from about 1.7% to about 2.3% of the composition.

10. Xanthan Gum

A cosmetic composition according to the present invention can further comprise xanthan gum as a thickener. For the moisturizing body lotion, xanthan gum preferably comprises from about 0.34% to about 0.46% of the composition.

11. The Complex of Dextran, Glycine, and Glucosamine

A cosmetic composition according to the present invention can further comprise a complex of dextran, glycine, and glucosamine. A suitable complex of dextran, glycine, and glucosamine comprises about 70% to about 90% of dextran, about 10% to about 20% of glycine, and about 5% to about 15% of glucosamine, and is marketed by Lab Serobiologique, Inc., under the name "Thalassamine LS-80/98." For the moisturizing body lotion, the complex of glucose, glycine, and glucosamine preferably comprises about 2.55% to about 3.45% of the composition.

12. The Glycosaminoglycan Complex

A cosmetic composition according to the present invention can further comprise a glycosaminoglycan complex. Preferably, the glycosaminoglycan complex is obtained from snail mucus. A suitable complex is marketed by Sederma, Inc. of Brooklyn, N.Y., under the name "Hydraprotectol." Preferably, for the exfoliating body slougher, the glycosaminoglycan complex comprises from about 2.55% to about 3.45% of the composition.

13. Magnesium Aluminum Silicate

A cosmetic composition according to the present invention can further comprise magnesium aluminum silicate. Preferably, for the exfoliating body slougher, magnesium aluminum silicate comprises from about 2.4% to about 3.2% of the composition.

14. The Cross-Polymer of Acrylates and $C_{10}$-$C_{30}$ Alkyl Acrylate

A cosmetic composition according to the present invention can further comprise a cross-polymer of acrylates and $C_{10}$–$C_{30}$ alkyl acrylate. For the cellulite firming gel, the cross-polymer preferably comprises from about 0.73% to about 0.98% of the composition.

15. Methylnicotinate

A cosmetic composition according to the present invention can further comprise methylnicotinate. For the cellulite firming gel, the methylnicotinate preferably comprises from about 0.05% to about 0.10% of the composition.

16. Triethanolamine

A cosmetic composition according to the present invention can further comprise triethanolamine. For the cellulite firming gel, the methylnicotinate preferably comprises from about 0.1% to about 0.2% of the composition.

The preferred concentrations of both the cosmetic components and the ancillary components are shown in Table I for an exfoliating body slougher according to the present invention, in Table II for a moisturizing body lotion according to the present invention, and in Table III for a cellulite firming gel according to the present invention. Also shown in Tables I, II and III are the mixtures of which each component is a part for the preparation of the compositions as discussed below.

TABLE I
INGREDIENTS OF A PREFERRED COSMETIC COMPOSITION ACCORDING TO THE PRESENT INVENTION (EXFOLIATING BODY SLOUGHER)

| Mixture Range | Component | Percentage |
|---|---|---|
| I | Demineralized Water | 16.50–22.50 |
| I | 1, 3-Butylene Glycol | 2.55–3.45 |
| I | Complex of Propylene Glycol, Phenoxyethanol, Chlorphenesin, and Methylparaben | 2.10–2.90 |
| I | Trisodium EDTA | 0.01–0.10 |
| II | Magnesium Aluminum Silicate | 2.40–3.20 |
| III | Complex of Glyceryl Stearate and PEG-100 Stearate | 11.50–15.50 |
| III | Tocopheryl Acetate | 0.05–0.15 |
| III | Complex of Glyceryl Linoleate, Glyceryl Linolenate, and Glyceryl Arachidonate | 0.05–0.15 |
| IV | Complex of Disodium Cocoamphodiacetate, Sodium Trideceth Sulfate, and Hexylene Glycol | 13.60–18.40 |
| V | Complex of Disodium Cocoamphodiacetate, Sodium Lauryl Sulfate, Sodium Laureth Sulfate, and Propylene Glycol | 17.00–23.00 |
| V | Polyquaternium-6 | 0.35–0.65 |
| V | Demineralized Water | 0.85–1.15 |
| VI | Aloe vera Gel | 0.35–0.65 |
| VII | Hydrophilic Microcapsules Comprising Glycerin, Chitin, Sodium Lactate, Sodium Pyrrolidone Carboxylic Acid, Glycogen, Urea, Propylene Glycol, Sodium Chloride, Glycine, Arginine, Lysine, Histidine, Ornithine, Placental Protein, Chlorphenesin, Methylparaben, and Water | 0.50–3.00 |
| VII | Hydrophobic Microcapsules Comprising Glycosphingolipids, Phospholipids, Cholesterol, Stearic acid, Palmitic acid, Squalane, $C_{10}$–$C_{30}$ Cholesterol/ Lanosterol Esters, Caprylic/ Capric Diglyceryl Succinate, and Octyldodecanol | 0.50–3.00 |
| VII | Firming Microcapsules Comprising Methylsilanol Elastinate and Water | 0.50–3.00 |
| VIII | Fragrance | 0.35–0.65 |
| IX | Polyethylene | 12.00–16.00 |
| X | FD&C Blue No. 1 | 0.001–0.05 |

TABLE II
INGREDIENTS OF A PREFERRED COSMETIC COMPOSITION ACCORDING TO THE PRESENT INVENTION (MOISTURIZING BODY LOTION)

| Mixture Range | Component | Percentage |
|---|---|---|
| I | Tocopheryl Acetate | 0.40–0.60 |
| I | Steareth-2 | 1.70–2.30 |
| I | Steareth-21 | 1.70–2.30 |
| I | Methylgluceth-20 Sesquistearate | 0.40–0.60 |
| I | Cetyl Alcohol | 1.70–2.30 |
| I | Jojoba Oil | 3.40–4.60 |
| I | Benzoic Acid Ester of $C_{12}$–$Cu_{15}$ Alcohols | 5.50–7.50 |
| I | PPG-14 Butyl Ether | 1.70–2.30 |
| I | Dimethicone | 0.15–0.25 |
| I | Complex of Sphingolipids, Phospholipids, and Octyldodecanol | 2.55–3.45 |
| I | Complex of Glyceryl Linoleate, Glyceryl Linolenate, and Glyceryl Arachidonate PPG-15 Stearyl Ether | 1.70–2.30 3.40–4.60 |
| II | Demineralized Water | 42.40–57.40 |
| II | Complex of Propylene Glycol, Phenoxyethanol, Chlorphenesin, and Methylparaben | 2.10–2.90 |
| III | Propylene Glycol | 4.25–5.75 |
| III | Xanthan Gum | 0.34–0.46 |
| IV | Demineralized Water | 2.55–3.45 |
| IV | Complex of Dextran, Glycine, and Glucosamine | 2.55–3.45 |
| IV | Glycosaminoglycan Complex | 2.55–3.45 |
| V | Hydrophilic Microcapsules comprising Glycerin, Chitin, Sodium Lactate, Sodium Pyrrolidone Carboxylic Acid, Glycogen, Urea, Propylene Glycol, Sodium Chloride, Glycine, Arginine, Lysine, Histidine, Ornithine, Placental Protein, Chlorphenesin, Methylparaben, and Water | 0.50–3.00 |
| V | Hydrophobic Microcapsules Comprising Glycosphingolipids, Phospholipids, Cholesterol, Stearic Acid, Palmitic Acid, Squalane, $C_{10}$–$C_{30}$ Cholesterol/ Lanosterol Esters, Caprylic/ Capric Diglyceryl Succinate, and Octyldodecanol | 0.50–3.00 |
| V | Firming Microcapsules Comprising Methylsilanol Elastinate and Water | 0.50–3.00 |
| VI | Aloe vera Gel | 0.40–0.60 |
| VI | Chamomile Extract | 0.40–0.60 |
| VII | Fragrance | 0.20–0.40 |

TABLE III
INGREDIENTS OF A PREFERRED COSMETIC COMPOSITION ACCORDING TO THE PRESENT INVENTION (CELLULITE FIRMING GEL)

| MIXTURE | COMPONENT | PERCENTAGE RANGE |
|---|---|---|
| I | Caffeine | 0.50–2.00 |
| I | Demineralized Water | 35.20–47.60 |
| II | Cross Polymer of Acrylates and $C_{10}C_{30}$ Alkyl Acrylate | 0.73–0.98 |
| III | Witch Hazel | 4.25–5.75 |
| III | Horsetail Extract | 0.85–1.15 |
| III | Ivy Extract | 0.85–1.15 |
| III | Chamomile Extract | 0.40–0.60 |
| III | Capsicum Extract | 2.55–3.45 |
| III | Vegetal Amino Complex Comprising Butcher Broom Extract, Propylene Glycol, Hydrocotyl Extract, Horse Chestnut Extract, Panthenol, Calendula Extract, and Yeast Extract | 0.85–1.15 |
| III | Comfrey Extract | 0.85–1.15 |
| III | Aloe vera Gel | 0.40–0.60 |
| III | Anti-Cellulite Microcapsules Comprising Methylsilanol Theophyllinacetate Alginate and Methylsilanol Mannuronate | 3.00–7.00 |

TABLE III-continued
INGREDIENTS OF A PREFERRED COSMETIC COMPOSITION ACCORDING TO THE PRESENT INVENTION (CELLULITE FIRMING GEL)

| MIXTURE | COMPONENT | PERCENTAGE RANGE |
|---|---|---|
| III | Firming Microcapsules Comprising Methylsilanol Elastinate and Water | 0.50–3.00 |
| III | Hydrophilic Microcapsules Comprising Glycerin, Chitin Sodium Lactate, Sodium Pyrrolidone Carboxylic Acid, Glycogen, Urea, Propylene Glycol, Sodium Chloride, Glycine, Arginine, Lysine, Histidine, Ornithine, Placental Protein, Phenoxyethanol, Chlorphenesin, Methylparaben, and Water | 0.50–3.00 |
| III | Hydrophobic Microcapsules Comprising Glycosphingolipids, Phospholipids, Cholesterol, Stearic Acid, Palmitic Acid Squalane, $C_{10}$-$C_{30}$ Cholesterol/Lanosterol Esters, Caprylic/Capric Diglyceryl Succinate, and Octyldodencanol | 0.50–3.00 |
| IV | Carrageenan | 0.35–0.55 |
| IV | Xanthan Gum | 0.25–0.45 |
| IV | 1,3-Butylene Glycol | 5.00–7.00 |
| IV | PPG-14 Isoceteth-3-Acetate | 3.40–4.60 |
| V | Laureth-2-Benzoate | 4.25–5.75 |
| V | Diisosteryl Dimer Dilinoleate | 1.25–1.75 |
| V | Myristyl Octanoate | 3.40–4.60 |
| V | Ascorbyl Palmitate | 0.01–0.03 |
| V | Tocopheryl Acetate | 0.40–0.60 |
| V | Complex of Glyceryl Linoleate, Glyceryl Linolenate, and Glyceryl Arachidonate | 0.40–0.60 |
| V | Glyceryl Stearate | 1.70–2.30 |
| V | Demineralized Water | 7.20–9.80 |
| VI | Complex of Phenoxyethanol, Methylparaben, Ethylparaben, Propylparaben, and Butylparaben | 0.64–0.86 |
| VII | Methylnicotinate | 0.05–0.10 |
| VII | Triethanolamine | 0.10–0.20 |
| VIII | Demineralized Water | 0.10–0.20 |
| IX | Fragrance | 0.20–0.60 |

II. PREPARATION OF COSMETIC COMPOSITIONS ACCORDING TO THE PRESENT INVENTION

The various mixtures and the sequences in which they are prepared and combined for the preparation of cosmetic compositions according to the present invention are now described in some detail, with reference to Tables I, II, and III.

A. Preparation of Exfoliating Body Slougher

Mixture I (demineralized water; 1,3-butylene glycol; the complex of propylene glycol, phenoxyethanol, chlorphenesin, and methylparaben; and trisodium EDTA) is introduced into a steam-jacketed stainless steel kettle equipped with a high-speed mixer such as a Lightnin' TM mixer and heated to 60° C. with vigorous mixing until clear. The temperature and mixing are maintained.

Mixture II (magnesium aluminum silicate) is sprinkled into the kettle containing Mixture I at 60° C. with vigorous mixing to form a gel and mixed until uniform, then set aside until later.

Mixture III (the complex of glyceryl stearate and PEG-100 stearate; tocopheryl acetate; and the complex of glyceryl linoleate, glyceryl linolenate, and glyceryl arachidonate) is charged into a steam-jacketed stainless steel kettle equipped with homogenization mixing and sweep mixing; the mixture is heated to 60° C. with moderate sweep mixing. Fast speed homogenization mixing is begun when the bulk is sufficiently liquefied. Temperature and mixing are maintained.

Mixture IV (the complex of disodium cocoamphodiacetate, trideceth sulfate, and hexylene glycol) is added at 60° C. to the batch kettle containing Mixtures I, II, and III with fast speed homogenization mixing for 10 min. until uniform, then cooled to 45° C. at the rate of 1° C./3 min.

Mixture V (the complex of disodium cocoamphodiacetate, sodium lauryl sulfate, sodium laureth sulfate, and propylene glycol; polyquaternium-6; and demineralized water) is mixed together separately with a high-speed mixer such as a Lightnin' TM mixture until clear, then added to the batch kettle at 40° C. with fast speed homogenization mixing and slow speed sweep mixing until uniform. Temperature and mixing are maintained.

Mixtures VI (Aloe vera gel and chamomile extract), VII (hydrophilic microcapsules, lipophilic microcapsules, and microcapsules comprising methylsilanol elastinate), and VIII (fragrance) are added to the batch kettle with fast speed homogenization mixing at 45° C. until uniform. Homogenization mixing is then discontinued and the batch cooled to 35°–40° C. with moderate sweep mixing.

Mixture IX (polyethylene) is then added to the batch kettle at 35°–40° C. with moderate sweep mixing for 1 hour until uniform.

The composition is colored to standard with Mixture X (FD & C Blue No. 1) with moderate sweep mixing, then cooled to 25° C. and filled into storage vessels for cold room storage (15°–20° C.).

B. Preparation of Moisturizing Body Lotion

Mixture I (tocopheryl acetate; the complex of glyceryl linoleate, glyceryl linolenate, and glyceryl arachidonate; and ten ingredients of the lipid-soluble component) is introduced into a steam-jacketed stainless steel kettle equipped with a high-speed mixer such as a Lightnin' TM mixer and heated to 70°–75° C. Vigorous mixing is begun when the bulk is sufficiently liquefied. Temperature and mixing are maintained.

Mixture II (demineralized water and the complex of propylene glycol, phenoxyethanol, chlorphenesin, and methylparaben) is charged into a steam-jacketed stainless steel kettle large enough to hold the entire batch and heated to 70°–75° C. with moderate sweep mixing until clear. Temperature and mixing are maintained.

Mixture I (the oil phase) is added at 70°–75° C. to the batch kettle containing Mixture II (the water phase). Fast speed homogenization mixing with slow sweep mixing is begun. Homogenization mixing is continued at 70°–75° C. for 30 min.

Mixture III (propylene glycol and xanthan gum) is pre-mixed to form a slurry, then added to the batch kettle at 70°–75° C. with fast speed homogenization mixing and slow sweep mixing for 30 min. until uniform. Homogenization mixing is then discontinued, and cooling of the batch is begun to 40°-45° C. with moderate sweep mixing; cooling is at a rate of 1° C./3 min.

Mixture IV (demineralized water; the complex of dextran, glycine, and glucosamine; and hydraprotectol) is pre-mixed until clear and then added to the batch kettle at 40°-45° C. with moderate sweep mixing until uniform.

Mixture V (hydrophilic microcapsules, lipophilic microcapsules, and microcapsules comprising methylsilanol elastinate) is added to the batch kettle at 40°-45° C. with moderate sweep mixing until uniform.

Mixtures VI (Aloe vera gel and chamomile extract) and VII (fragrance) are added to the batch kettle at 40°-45° C. with moderate sweep mixing until uniform. The batch is cooled with slow sweep mixing to 25° C. and filled into storage vessels for cold room storage (15°-20° C.).

C. Preparation of Cellulite Firming Gel

Mixture I (caffeine and demineralized water) is pumped into a stainless steel kettle equipped with a high-speed mixer and heated to 60°-65° with vigorous mixing until clear. Mixture II (the cross-polymer of acrylates and $C_{10}-C_{30}$ alkyl acrylate) is added to Mixture I with vigorous propeller mixing. The cross-polymer typically takes an entire day to dissolve, and the sides and bottom of the kettle should be scraped frequently to remove cross-polymer that adhere to the kettle. The combination of Mixtures I and II is allowed to sit covered overnight and mixing is begun again the next morning.

Mixture V (demineralized water, eight ingredients of the lipid-soluble component, ascorbyl palmitate, tocopheryl acetate, and the glyceryl ester complex) is loaded into a separate stainless steel kettle equipped with sweep mixing and homogenization mixing. The mixture is heated to 60°-65° C. with moderate sweep mixing. When melted, the mixture is mixed with slow speed homogenization mixing for 30 minutes. Homogenization mixing is then discontinued, and the mixture is pumped out into a stainless steel drum and covered; the mixture is stored in a hot room at 60° overnight.

After the kettle used for Mixture V is cleaned, Mixture III (witch hazel, horsetail extract, ivy extract, chamomile extract, capsicum extract, vegetal amino complex, comfrey extract, *Aloe vera* gel, and the four types of microcapsules) is loaded into the kettle and mixed with sweep mixing until uniform. Mixture IV (carrageenan, xanthan gum, and 1,3-butylene glycol) is premixed in a separate container with a propeller mixer. Mixture IV is then added to Mixture III with vigorous mixing, and fast homogenization mixing with moderate sweep mixing is performed for approximately 90 minutes until the combination is smooth. The bottom of the kettle should be checked for complete dispersion. Homogenization mixing is then discontinued, and slow sweep mixing is continued until the end of the day. The combination of Mixtures III and IV is then allowed to sit in the kettle overnight. All these steps are to be completed on the first day of manufacture.

On the second day, Mixture V is removed from the hot room and mixed with a propeller mixer until homogenous; if the mixture is not completely melted, it is to be reheated to 60°-65° C. with propeller mixing.

Mixture V is then pumped into the kettle containing Mixtures III and IV. During pumping, slow speed homogenization mixing is performed. When pumping is complete, moderate sweep mixing and fast homogenization mixing are performed for 30-60 minutes until the combination of Mixtures III, IV, and V is smooth. Homogenization mixing is then discontinued.

Before being added, the combination of Mixtures I and II must be smooth, homogenous, and free of lumps. The combination of Mixtures I and II is then pumped into the kettle containing a combination of Mixtures III, IV, and V. Fast sweep mixing is performed for 60 minutes.

The batch is then run through a Gaulin homogenizer at a setting of 1000 psi into stainless steel drums. The kettle is then cleaned, and the batch is pumped into it.

Mixtures VI (the complex of phenoxyethanol, methylparaben, ethylparaben, propylparaben, and butylparaben) and VII (methylnicotinate) are added to the batch with moderate sweep mixing; mixing is continued for 30 minutes.

Mixture VIII (triethanolamine and demineralized water) is premixed and added to the batch. The batch is then mixed with sweep mixing at fast speed for 60 minutes until the batch is homogeneous.

Mixture IX (fragrance) is then added to the batch kettle with sweep mixing at moderate speed until the batch is uniform. At this point, sweep mixing is to be discontinued completely. The batch is then dropped from the kettle into tightly sealed stainless steel drums and stored in the cold room.

ADVANTAGES OF THE INVENTION

Cosmetic compositions according to the present invention simultaneously provide totally comprehensive hydrating, protecting, soothing, and anti-free radical activity, plus firming or anti-cellulite activity, or both, according to the microcapsules used in the particular composition. The use of microcapsules provides for long term sustained release of the active ingredients, giving significantly longer duration of activity. The use of both hydrophilic and lipophilic microcapsules provides comprehensive moisturizing, addressing both water and lipid shortages of the skin. Most moisturizers address water shortage, some address lipid shortage, but so far no one has addressed both using a slow release, long term mechanism for addressing both. This is accomplished together with providing firming, anti-cellulite and anti-free radical effects in some formulations where necessary.

Although the present invention has been described in considerable detail with regard to certain preferred versions thereof, other versions are possible. Therefore, the spirit and scope of the appended claims should not be limited to the description of the preferred versions contained herein.

I claim:

1. A cosmetic composition comprising: water, and emulsified and dispersed in the water:
   (a) a moisturizing component comprising:
      (i) hydrophilic microcapsules comprising in water: (1) glycerin, (2) chitin, (3) sodium lactate, (4) sodium chloride, (5) sodium pyrrolidone carboxylate, (6) glycogen, (7) urea, (8) propylene glycol, and (9) at least one amino acid selected from the group of amino acids consisting of glycine, arginine, lysine, histidine, and ornithine; and
      (ii) lipophilic microcapsules comprising (1) octyldodecanol, (2-glycosphingolipids, (3) phospholipids, (4) cholesterol, (5) at least one long-chain saturated fatty acid selected from the group consisting of myristic acid, palmitic acid, stearic acid, and arachidic acid, (6) squalene, and (7) a $C_{10}$–$C_{30}$ carboxylic acid ester of a sterol selected from the group consisting of cholesterol, lanosterol, and mixtures thereof;
(b) a short-chain fatty acid ester of tocopherol selected from the group consisting of tocopheryl acetate, tocopheryl propionate, tocopheryl butyrate, and mixtures thereof;
(c) a glyceryl ester complex comprising at least one ingredient selected from the group consisting of glyceryl linoleate, glyceryl linolenate, and glyceryl arachidonate;
(d) Aloe vera gel; and
(e) chamomile extract;
the proportion of hydrophilic microcapsules to lipophilic microcapsules in the moisturizing component being from about 2:3 to about 3:2.

2. The cosmetic composition of claim 1 further comprising:
(f) microcapsules comprising methylsilanol elastinate.

3. The cosmetic composition of claim 1 further comprising:
(f) caffeine; and
(g) microcapsules comprising methylsilanol theophyllinacetate alginate.

4. The cosmetic composition of claim 1 further comprising:
(f) microcapsules comprising in water:
  (i) methylsilanol theophyllinacetate alginate; and
  (ii) methylsilanol mannuronate; and
(g) caffeine;

5. The cosmetic composition of claim 2 further comprising:
(f) microcapsules comprising in water:
  (i) methylsilanol theophyllinacetate alginate;
  (ii) methylsilanol mannuronate; and
(g) caffeine.

6. The cosmetic composition of claim 1 wherein the hydrophilic microcapsules further comprise placental protein.

7. The cosmetic composition of claim 1 wherein the hydrophilic microcapsules further comprise at least one preservative component selected from the group consisting of phenoxyethanol, chlorphenesin, and methylparaben.

8. The cosmetic composition of claim 6 wherein the hydrophilic microcapsules comprise all of phenoxyethanol, chlorphenesin, and methylparaben.

9. The cosmetic composition of claim 1 wherein the hydrophilic microcapsules comprise all of glycine, arginine, lysine, histidine, and ornithine.

10. The cosmetic composition of claim 1 wherein the lipophilic microcapsules further comprise a diglyceryl succinate of a medium-chain fatty acid selected from the group consisting of caprylic acid, capric acid, and mixtures thereof.

11. The cosmetic composition of claim 3 further comprising:
(g) a mixture of plant extracts and plant extract-miscible components comprising:
  (i) witch hazel;
  (ii) horsetail extract;
  (iii) ivy extract;
  (iv) capsicum extract;
  (v) a vegetal amino complex comprising from about 25% to about 35% of butcher broom extract; about 25% to about 35% of propylene glycol, about 5% to about 15% each of hydrocotyl extract, horse chestnut extract, and panthenol, about 4% to about 8% of calendula extract, and about 3% to about 6% of yeast extract; and
  (vi) comfrey extract; and
(h) a long-chain saturated fatty acid ester of ascorbic acid.

12. The cosmetic composition of claim 4 further comprising:
(i) witch hazel;
(ii) horsetail extract;
(iii) ivy extract;
(iv) capsicum extract;
(v) a vegetal amino complex comprising from about 25% to about 35% of butcher broom extract; about 25% to about 35% of propylene glycol, about 5% to about 15% each of hydrocotyl extract, horse chestnut extract, and panthenol, about 4% to about 8% of calendula extract, and about 3% to about 6% of yeast extract; and
(vi) comfrey extract; and
(h) a long-chain saturated fatty acid ester of ascorbic acid.

13. The cosmetic composition of claim 1 wherein the moisturizing component comprises from about 0.5% to about 3% of the composition, the short-chain fatty acid ester of tocopherol comprise from about 0.05% to about 1% of the composition, the glyceryl ester complex comprises from about 0.05% to about 2.5% of the composition, the Aloe vera gel comprises from about 0.1% to about 1% of the composition, and the chamomile extract comprises from about 0.1% to about 1% of the composition.

14. The cosmetic composition of claim 13 further comprising:
(f) microcapsules comprising methylsilanol elastinate, the microcapsules comprising methylsilanol elastinate comprising from about 0.5% to about 3% of the composition.

15. The cosmetic composition of claim 14 further comprising:
(g) microcapsules comprising in water:
  (i) methylsilanol theophyllinacetate alginate; and
  (ii) methylsilanol mannuronate; and
(f) caffeine; the microcapsules comprising methylsilanol theophyllinacetate alginate and methylsilanol mannuronate comprising from about 3% to about 7% of the composition and the caffeine comprising from about 0.5% to about 2% of the composition.

16. The cosmetic composition of claim 1 wherein:
(a) the hydrophilic microcapsules comprise:
  (i) from about 20% to about 40% glycerin;
  (ii) from about 10% to about 20% chitin;
  (iii) from about 5% to about 15% sodium lactate;
  (iv) from about 5% to about 15% sodium pyrrolidone carboxylate;
  (v) from about 1% to about 5% each of glycogen, urea, propylene glycol, and sodium chloride;
  (vi) up to about 1% each of glycine, arginine, lysine, histidine, ornithine, placental protein, phenoxyethanol, and chlorphenesin; and
  (vii) up to about 0.5% of methylparaben;
(b) the lipophilic microcapsules comprise:
  (i) from about 5% to about 15% each of glycosphingolipids, phospholipids, and cholesterol;
  (ii) from about 1% to about 5% each of stearic acid, palmitic acid, squalane, and a $C_{10}$–$C_{30}$ carboxylic acid ester of a sterol selected from the group consisting of cholesterol, lanosterol, and mixtures thereof;

(iii) up to about 1% of a diglyceryl succinate of a medium-chain fatty acid selected from the group consisting of caprylic acid, capric acid, and mixtures thereof; and (iv) from about 60% to about 80% of octyldodecanol;

the moisturizing component comprising from about 0.5% to about 3% of the composition;

(c) the short-chain fatty acid ester of tocopherol comprises from about 0.5% to about 1.% of the composition;

(d) the glyceryl ester complex comprises from 0.5% to about 2.5% of the composition;

(e) the *Aloe vera* gel comprises from about 0.1% to about 1% of the composition; and (f) the chamomile extract comprises from about 0.1% to about 1% of the composition.

17. The cosmetic composition of claim 16 further comprising:

(g) microcapsules comprising methylsilanol elastinate, the microcapsules comprising methylsilanol elastinate comprising from about 0.5% to about 3% of the composition.

18. The cosmetic composition of claim 17 further comprising:

(h) microcapsules comprising from about 40% to about 60% methylsilanol theophyllinacetate alginate and from about 40% to about 60% of methylsilanol mannuronate in water, the microcapsules comprising from about 3% to about 7% of the composition; and (i) caffeine comprising from about 0.5% to about 2% of the composition.

19. The cosmetic composition of claim 1 further comprising at least one of:

(f) a lipid-soluble component comprising at least one of the following ingredients: (a) steareth-2; (b) steareth-21; (c) methylgluceth-20 sesquistearate; (d) cetyl alcohol; (e) jojoba oil; (f) benzoic acid ester of $C_{12}$–$C_{15}$ alcohols; (g) PPG-14 butyl ether; (h) PPG-15 stearyl ether; (i) dimethicone; (j) a complex of sphingolipids, phospholidpis, and octyloddecanol; (k) a complex of glyceryl stearate and PEG-100 stearate; (l) PPG-1-isoceteth-3-acetate; (m) laureth-2-benzoate; (n) diisostearyl dimer dilinoleate; (o) a long-chain cis-monounsaturated fatty acid ester of a medium-chain alcohol; (p) a medium-chain saturated fatty acid ester of a long-chain alcohol; and (q) a long-chain fatty acid ester of glycerol;

(g) a solvent component selected from the group of solvents consisting of propylene glycol, 1,3-butylene glycol, and mixtures thereof;

(h) a complex of dextran, glycine, and glucosamine, wherein the dextran comprises from about 70% to about 90% of the complex, the glycine comprises from about 10% to about 20% of the complex, and the glucosamine comprises from about 5% to about 15% of the complex;

(i) a preservative component comprising a complex of propylene glycol, phenoxyethanol, chlorphenesin, and methylparaben; or a complex of phenoxyethanol, methylparaben, ethylparaben, propylparaben, and butylparaben;

(j) trisodium EDTA;

(k) a thickener component;

(l) an emulsifier component comprising a complex of disodium cocoamphodiacetate, sodium lauryl sulfate, sodium laureth sulfate, and propylene glycol; and a complex of disodium cocoamphodiacetate, sodium trideceth sulfate, and hexylene glycol;

(m) magnesium aluminum silicate;

(n) a cationic dimethyldiallyl ammonium chloride homopolymer;

(o) a glycosaminoglycan complex;

(p) polyethylene;

(q) pigment;

(r) fragrance;

(s) a cross-polymer of acrylates and $C_{10}$–$C_{30}$ alkyl acrylate;

(t) methylnicotinate; and (u) triethanolamine.

20. A cosmetic composition comprising: water, and emulsified and dispersed in the water:

(a) a moisturizing component comprising:

(i) hydrophilic microcapsules comprising in water:

(A) glycerin;
(B) chitin;
(C) sodium lactate;
(D) sodium pyrrolidone carboxylate;
(E) glycogen;
(F) urea;
(G) propylene glycol;
(H) sodium chloride;
(I) glycine;
(J) arginine;
(K) lysine;
(L) histidine;
(M) ornithine;
(N) placental protein;
(O) phenoxyethanol;
(P) chlorphenesin; and
(Q) methylparaben; and (ii) lipophilic microcapsules comprising:

(A) glycosphingolipids;
(B) phospholipids;
(C) cholesterol;
(D) stearic acid;
(E) palmitic acid;
(F) squalene;
(G) a $C_{10}$–$C_{30}$ carboxylic acid ester of a sterol selected from the group consisting of cholesterol, lanosterol, and mixtures thereof;
(H) a diglyceryl succinate of a medium-chain fatty acid selected from the group consisting of caprylic acid, capric acid, and mixtures thereof; and
(I) octyldodecanol; the proportion of hydrophilic microcapsules to lipophilic microcapsules being from about 2:3 to about 3:2;

(b) tocopheryl acetate;

(c) a glyceryl ester complex comprising about 65% to about 85% of glyceryl linoleate, about 5% to about 15% of glyceryl arachidonate;

(d) Aloe vera gel;

(e) chamomile extract;

(f) microcapsules comprising methylsilanol elastinate;

(g) 1,3-butylene glycol;

(h) a complex of propylene glycol, phenoxyethanol, chlorphenesin, and methylparaben, wherein the propylene glycol comprises from about 30% to about 45% of the complex, the phenoxyethanol comprises from about 22% to about 37% of the complex, the chlorphenesin comprises from about 11% to about 22% of the complex, and the methylparaben comprises from about 11% of about 22% of the complex;
(i) trisodium EDTA;
(j) magnesium aluminum silicate;
(k) an emulsifier component comprising:
   (i) a complex of disodium cocoamphodiacetate, sodium lauryl sulfate, sodium laureth sulfate, and propylene glycol; and
   (ii) a complex of disodium cocoamphodiacetate, sodium trideceth sulfate, and hexylene glycol;
(l) a lipid-soluble component comprising a complex of glyceryl stearate and PEG-100 stearate, wherein the glyceryl stearate comprises from about 40% to about 60% of the complex and the PEG-100 stearate comprises from about 40% to about 60% of the complex;
(m) a cationic dimethyldiallyl ammonium chloride homopolymer;
(n) fragrance;
(o) polyethylene; and
(p) FD & C Blue No. 1.

21. A cosmetic composition comprising: water, and emulsified and dispersed in the water;
(a) a moisturizing component comprising:
   (i) hydrophilic microcapsules comprising in water:
     (A) glycerin;
     (B) chitin;
     (C) sodium lactate;
     (D) sodium pyrrolidone carboxylate;
     (E) glycogen;
     (F) urea;
     (G) propylene glycol;
     (H) sodium chloride;
     (I) glycine;
     (J) arginine;
     (K) lysine;
     (L) histidine;
     (M) ornithine;
     (N) placental protein;
     (O) phenoxyethanol;
     (P) chlorphenesin; and
     (Q) methylparaben; and
   (ii) lipophilic microcapsules comprising:
     (A) glycosphingolipids;
     (B) phospholipids;
     (C) cholesterol;
     (D) stearic acid;
     (E) palmitic acid;
     (F) squalene;
     (G) a $C_{10}$–$C_{30}$ carboxylic acid ester of a sterol selected from the group consisting of cholesterol, lanosterol, and mixtures thereof;
     (H) a diglyceryl succinate of a medium-chain fatty acid selected from the group consisting of caprylic acid, capric acid, and mixtures thereof; and
     (I) octyldodecanol; the proportion of hydrophilic microcapsules to lipophilic microcapsules being from about 2:3 to about 3:2;
(b) tocopheryl acetate present in a cosmetically effective quantity;
(c) a glyceryl ester complex comprising about 65% to about 85% of glyceryl linoleate, about 5% to about 15% of glyceryl linolenate, and about 1% to about 5% of glyceryl arachidonate;
(d) Aloe vera gel;
(e) chamomile extract;
(f) microcapsules comprising methylsilanol elastinate;
(g) propylene glycol;
(h) a complex of propylene glycol, phenoxyethanol, chlorphenesin, and methylparaben, wherein the propylene glycol comprises from about 30% to about 45% of the complex, the phenoxyethanol comprises from about 22% to about 37% of the complex, the chlorphenesin comprises from about 11% to about 22% of the complex, and the methylparaben comprises from about 11% to about 22% of the complex;
(i) a lipid-soluble component comprising:
   (i) steareth-2;
   (ii) steareth-21;
   (iii) methylgluceth-20 sesquistearate;
   (iv) cetyl alcohol;
   (v) jojoba oil;
   (vi) benzoic acid ester of $C_{12}$–$C_{15}$ alcohols;
   (vii) PPG-14 butyl ether;
   (viii) dimethicone;
   (ix) a complex of sphingolipids, phospholipids, and octyldodecanol; and
   (x) PPG-15 stearyl ether;
(j) xanthan gum;
(k) a complex of dextran, glycine, and glucosamine, wherein the dextran comprises from about 70% to about 90% of the complex, the glycine comprises from about 10% to about 20% of the complex, and the glucosamine comprises from about 5% to about 15% of the complex;
(l) a glycosaminoglycan complex; and
(m) fragrance.

22. A cosmetic composition comprising: water, and emulsified and dispersed in the water;
(a) a moisturizing component comprising:
   (i) hydrophilic microcapsules comprising from about 0.5% to about 3% of the composition, the hydrophilic microcapsules comprising in water:
     (A) about 20% to about 40% glycerin;
     (B) about 10% to about 20% chitin;
     (C) about 5% to about 15% each of sodium lactate and sodium pyrrolidone carboxylic acid;
     (D) about 1% to about 5% each of glycogen, urea, propylene glycol, and sodium chloride;
     (E) up to about 1% each of glycine, arginine, lysine, histidine, and ornithine, such that at least one amino acid is present in the hydrophilic microcapsules;
     (F) up to about 1% each of placental protein, phenoxyethanol, and chlorphenesin; and
     (G) up to about 0.5% of methylparaben; and
   (ii) lipophilic microcapsules comprising from about 0.5% to about 3% of the composition, the lipophilic microcapsules comprising:
     (A) about 5% to about 15% each of glycosphingolipids, phospholipids, and cholesterol;
     (B) about 1% to about 5% each of stearic acid, palmitic acid, squalane, and a $C_{10}$–$C_{30}$ carboxylic acid ester of a sterol selected from the group consisting of cholesterol, lanosterol, and mixtures thereof;
     (C) up to about 1% of a diglyceryl succinate of a medium-chain fatty acid selected from the group consisting of caprylic acid, capric acid, and mixtures thereof; and
     (D) about 60% to about 80% of octyldodecanol; the quantities of hydrophilic microcapsules and lipophilic microcapsules being such that the ratio of hydrophilic microcapsules to lipophilic microcapsules is from about 2:3 to about 3:2;

(b) about 0.5% to about 3% of microcapsules comprising methylsilanol elastinate;

(c) about 2.55% to about 3.45% of 1,3-butylene glycol;

(d) about 2.1% to about 2.9% of a complex of propylene glycol, phenoxyethanol, chlorphenesin, and methylparaben, wherein the propylene glycol comprises from about 30% to about 45% of the complex, the phenoxyethanol comprises from about 22% to about 37% of the complex, the chlorphenesin comprises from about 11% to about 22% of the complex, and the methylparaben comprises from about 11% to about 22% of the complex;

(e) about 0.01% to about 0.1% of trisodium EDTA;

(f) about 2.4% to about 3.2% of magnesium aluminum silicate;

(g) about 11.5% to about 15.5% of a complex of glyceryl stearate and PEG-100 stearate, wherein the glyceryl stearate comprises from about 40% to about 60% of the complex and the PEG-100 stearate comprises from about 40% to about 60% of the complex;

(h) about 0.05% to about 0.15% of tocopheryl acetate;

(i) about 0.05% to about 0.15% of a glyceryl ester complex comprising about 65% to about 85% of glyceryl linoleate, about 5% to about 15% of glyceryl linolenate, and about 1% to about 5% of glyceryl arachidonate;

(j) about 13.6% to about 18.4% of a complex comprising disodium cocoamphodiacetate, sodium trideceth sulfate, and hexylene glycol;

(k) about 17% to about 23% of a complex comprising disodium cocoamphodiacetate, sodium lauryl sulfate, sodium laureth sulfate, and propylene glycol;

(l) about 0.35% to about 0.65% of a cationic dimethyldiallyl ammonium chloride homopolymer;

(m) about 0.35% to about 0.65% of *Aloe vera* gel;

(n) about 0.35% to about 0.65% of chamomile extract;

(o) about 0.35% to about 0.65% of fragrance;

(p) about 12% to about 16% of polyethylene; and (q) about 0.01% to about 0.05% of FD & C Blue No. 1.

23. A cosmetic composition comprising: water, and emulsified and dispersed in the water:

(a) a moisturizing component comprising:

(i) hydrophilic microcapsules, the hydrophilic microcapsules comprising from about 0.5% to about 3% of the composition, the hydrophilic microcapsules comprising in water:

(A) about 20% to about 40% glycerin;

(B) about 10% to about 20% chitin;

(C) about 5% to about 15% each of sodium lactate and sodium pyrrolidone carboxylic acid;

(D) about 1% to about 5% each of glycogen, urea, propylene glycol, and sodium chloride;

(E) up to about 1% each of glycine, arginine, lysine, histidine, and ornithine, such that at least one amino acid is present in the hydrophilic microcapsules;

(F) up to about 1% each of placental protein, phenoxyethanol, and chlorphenesin; and (G) up to about 0.5% of methylparaben; and (ii) lipophilic microcapsules comprising from about 0.5% to about 3% of the composition, the lipophilic microcapsules comprising:

(A) about 5% to about 15% each of glycosphingolipids, phospholipids, and cholesterol;

(B) about 1% to about 5% each of stearic acid, palmitic acid, squalane, and a $C_{10}$–$C_{30}$ carboxylic acid ester of a sterol selected from the group consisting of cholesterol, lanosterol, and mixtures thereof;

(C) up to about 1% of a diglyceryl succinate of a medium-chain fatty acid selected from the group consisting of caprylic acid, capric acid, and mixtures thereof; and (D) about 60% to about 80% of octyldodecanol; the quantities of hydrophilic microcapsules and lipophilic microcapsules being such that the ratio of hydrophilic microcapsules to lipophilic microcapsules is from about 2:3 to about 3:2;

(b) about 0.5% to about 3% of microcapsules comprising methylsilanol elastinate;

(c) about 0.4% to about 0.6% of tocopheryl acetate;

(d) about 1.7% to about 2.3% of steareth-2;

(e) about 1.7% to about 2.3% of steareth-21;

(f) about 0.4% to about 0.6% of methylgluceth-20 sesquistearate;

(g) about 1.7% to about 2.3% of cetyl alcohol;

(h) about 3.4% to about 4.6% of jojoba oil; (i) about 5.5% to about 7.5% of benzoic acid ester of $C_{12}$–$C_{15}$ alcohol;

(i) about 1.7% to about 2.3% of PPG-14 butyl ether;

(j) about 0.15% to about 0.25% of dimethicone;

(k) about 2.55% to about 3.45% of a complex of sphingolipids, phospholipids, and octyldodecanol, wherein the sphingolipids comprise about 10% to about 19% of the complex, the phospholipids comprise from about 10% to about 19% of the complex, and the octyldodecanol comprises from about 60% to about 80% of the complex;

(l) about 1.7% to about 2.3% of a glyceryl ester complex comprising about 65% to about 85% of glyceryl linoleate, about 5% to about 15% of glyceryl linolenate, and about 1% to about 5% of glyceryl arachidonate;

(m) about 3.4% to about 4.6% of PPG-15 stearyl ether; (n) about 2.1% to about 2.9% of a complex of propylene glycol, phenoxyethanol, chlorphenesin, and methylparaben, wherein the propylene glycol comprises from about 30% to about 45% of the complex, the phenoxyethanol comprises from about 22% to about 37% of the complex, the chlorphenesin comprises from about 11% to about 22% of the complex, and the methylparaben comprises from about 11% to about 22% of the complex;

(o) about 4.25% to about 5.75% of propylene glycol;

(p) about 0.34% to about 0.46% of xanthan gum;

(q) about 2.55% to about 3.45% of a complex of dextran, glycine, and glucosamine, wherein the dextran comprises from about 70% to about 90% of the complex, the glycine comprises from about 10% to about 20% of the complex, and the glucosamine comprises from about 5% to about 15% of the complex;

(r) about 2.55% to about 3.45% of a glycosaminoglycan complex;

(s) about 0.4% to about 0.6% of *Aloe vera* gel;

(t) about 0.4% to about 0.6% of chamomile extract; and (u) about 0.2% to about 0.4% of fragrance.

24. A cosmetic composition comprising: water, and emulsified and dispersed in the water:
(a) a moisturizing component comprising:
(i) hydrophilic microcapsules comprising in water:
(A) glycerin;
(B) chitin;
(C) sodium lactate;
(D) sodium pyrrolidone carboxylate;
(E) glycogen;
(F) urea;
(G) propylene glycol;
(H) sodium chloride;
(I) glycine
(J) arginine;
(K) lysine;
(L) histidine;
(M) ornithine;
(N) placental protein;
(O) phenoxyethanol;
(P) chlorphenesin; and
(Q) methylparaben; and
(ii) lipophilic microcapsules comprising:
(A) glycosphingolipids;
(B) phospholipids;
(C) cholesterol;
(D) stearic acid;
(E) palmitic acid;
(F) squalene;
(G) a $C_{10}$–$C_{30}$ carboxylic acid ester of a sterol selected from the group consisting of cholesterol, lanosterol, and mixtures thereof;
(H) a diglyceryl succinate of a medium-chain fatty acid selected from the group consisting of caprylic acid, capric acid, and mixtures thereof; and
(I) octyldodecanol; the proportion of hydrophilic microcapsules to lipophilic microcapsules being from about 2:3 to about 3:2;
(b) tocopheryl acetate;
(c) a glyceryl ester complex comprising from about 65% to about 85% of glyceryl linoleate, about 5% to about 15% of glyceryl linolenate, and from about 1% to about 5% of glyceryl arachidonate;
(d) Aloe vera gel;
(e) chamomile extract;
(f) microcapsules comprising methylsilanol elastinate;
(g) microcapsules present in a and comprising in water:
(i) methylsilanol theophyllinacetate alginate; and
(ii) methylsilanol mannuronate;
(h) caffeine;
(i) a mixture of plant extracts and plant extract miscible components and comprising:
(i) witch hazel;
(ii) horsetail extract;
(iii) ivy extract;
(iv) capsicum extract;
(v) a vegetal amino complex comprising from about 25% to about 35% of butcher broom extract, from about 25% to about 35% of propylene glycol, from about 5% to about 15% each of hydrocotyl extract, horse chestnut extract, and panthenol, from about 4% to about 8% of calendula extract, and about 3% to about 6% of yeast extract; and (vi) comfrey extract;
(j) ascorbyl palmitate;
(k) a cross-polymer of acrylates and $C_{10}$–$C_{30}$ alkyl acrylate;
(l) a thickener component comprising:
(i) carrageenan; and
(ii) xanthan gum;
(m) a lipid-soluble component comprising:
(i) PPG-1-isoceteth-3-acetate;
(ii) laureth-2-benzoate;
(iii) diisostearyl dimer dilinoleate;
(iv) isodecyl oleate;
(v) myristyl octanoate; and
(vi) glyceryl stearate;
(n) 1,3-butylene glycol;
(o) a complex of phenoxyethanol, ethylparaben, ethylparaben, propylparaben, and butylparaben, with the phenoxyethanol comprising from about 60% to about 80% of the complex, the methylparaben comprising from about 13% to about 17% of the complex, and the ethylparaben, propylparaben, and butylparaben each comprising from about 4% to about 6% of the complex;
(p) methylnicotinate;
(q) triethanolamine; and
(r) fragrance.

25. A cosmetic composition comprising: water, and emulsified and dispersed in the water;
(a) a moisturizing component comprising:
(i) hydrophilic microcapsules comprising from about 0.5% about 3% of the composition, the hydrophilic microcapsules comprising in water;
(A) from about 20% to about 40% glycerin;
(B) from about 10% to about 20% chitin;
(C) from about 5% to about 15% each of sodium lactate and sodium pyrrolidone carboxylate;
(D) from about 1% to about 5% each of glycogen, urea, propylene glycol, and sodium chloride;
(E) up to about 1% each of glycine, arginine, lysine, histidine, and ornithine, such that at least one amino acid is present in the hydrophilic microcapsules;
(F) up to about 1% each of placental protein, phenoxyethanol, and chlorphenesin; and
(G) up to about 0.5% of methylparaben; and
(ii) lipophilic microcapsules comprising from about 0.5% to about 3% of the composition, the lipophilic microcapsules comprising:
(A) from about 5% to about 15% each of glycosphingolipids, phospholipids, and cholesterol;
(B) from about 1% to about 5% each of stearic acid, palmitic acid, squalene, and a $C_{10}$–$C_{30}$ carboxylic acid ester of a sterol selected from the group consisting of cholesterol, lanosterol, and mixtures thereof; and
(C) up to about 1% of a diglyceryl succinate of a medium-chain fatty acid selected from the group consisting caprylic acid, capric acid, and mixtures thereof; and
(D) from about 60% to about 80% of octyldodecanol;
the quantities of hydrophilic microcapsules and lipophilic microcapsules being such that the ratio of hydrophilic microcapsules to lipophilic microcapsules is from about 2:3 to about 3:2;
(b) from about 0.4% to about 0.6% of tocopheryl acetate;

(c) from about 0.4% to about 0.6% of a glyceryl ester complex comprising from about 65% to about 85% of glyceryl linoleate, from about 5% to about 15% of glyceryl linolenate, and from about 1% to about 5% of glyceryl arachidonate;

(d) from about 0.4% to about 0.6% of Aloe vera gel;

(e) from about 0.4% to about 0.6% of chamomile extract;

(f) from about 0.5% to about 3% of microcapsules comprising methylsilanol elastinate;

(g) from about 3% to about 7% of microcapsules comprising in water:
 (i) from about 40% to about 60% methylsilanol theophyllinacetate alginate; and
 (ii) from about 40% to about 60% methylsilanol mannuronate;

(h) from about 0.5% to about 2% of caffeine;

(i) from about 4.25% to about 5.75% of witch hazel;

(j) from about 0.85% to about 1.15% of horsetail extract;

(k) from about 0.85% to about 1.15% of ivy extract;

(l) from about 2.55% to about 3.45% of capsicum extract;

(m) from about 0.85% to about 1.15% of a vegetal amino complex comprising from about 25% to about 35% of butcher broom extract, from about 25% to about 35% of propylene glycol, from about 5% to about 15% each of hydrocotyl extract, horse chestnut extract, and panthenol, from about 4% to about 8% of calendula extract, and from about 3% to about 6% of yeast extract;

(n) from about 0.85% to about 1.15% of ascorbyl palmitate;

(o) from about 0.73% to about 0.98% of a crosspolymer of acrylates and $C_{10}$–$C_{30}$ alkyl acrylate;

(p) from about 0.35% to about 0.55% of carrageenan;

(q) from about 0.25% to about 0.45% of xanthan gum;

(r) from about 5% to about 7% of 1,3-butylene glycol;

(s) from about 3.4% to about 4.6% of PPG-1-isoceteth-3-acetate;

(t) from about 4.2% to about 5.75% of laureth-2-benzoate;

(u) from about 1.25% to about 1.75% of diisostearyl dimer dilinoleate;

(v) from about 1.25% to about 1.75% of isodecyl oleate; (w) from about 3.4% to about 4.6% of myristyl octanoate;

(x) from about 0.1% to about 0.3% of ascorbyl palmitate;

(y) from about 1.7% to about 2.3% of glyceryl stearate;

(z) from about 0.64% to about 0.8% of a complex of phenoxyethanol, methylparaben, ethylparaben, propylparaben, and butylparaben, with the phenoxyethanol comprising from about 60% to about 80% of the complex, the methylparaben comprising from about 13% to about 17% of the complex, and the ethylparaben, propylparaben, and butylparaben each comprising from about 4% to about 6% of the complex;

(aa) from about 0.05% to about 0.1% of methylnicotinate;

(bb) from about 0.1% to about 0.2% of triethanolamine; and (cc) from about 0.2% to about 0.6% of fragrance.

* * * * *